(12) United States Patent
Frank (10) Patent No.: US 12,154,272 B2
(45) Date of Patent: Nov. 26, 2024

(54) DIGITAL TISSUE SEGMENTATION AND MAPPING WITH CONCURRENT SUBTYPING

(71) Applicant: Steven J Frank, Framingham, MA (US)

(72) Inventor: Steven J Frank, Framingham, MA (US)

(*) Notice: Subject to any disclaimer, the term of this patent is extended or adjusted under 35 U.S.C. 154(b) by 262 days.

(21) Appl. No.: 17/871,878

(22) Filed: Jul. 22, 2022

(65) Prior Publication Data

US 2023/0050168 A1 Feb. 16, 2023

Related U.S. Application Data

(63) Continuation-in-part of application No. 17/402,524, filed on Aug. 14, 2021.

(60) Provisional application No. 63/331,265, filed on Apr. 15, 2022.

(51) Int. Cl.
| | | |
|---|---|---|
| *G06T 7/00* | (2017.01) | |
| *G06T 7/11* | (2017.01) | |
| *G06V 10/22* | (2022.01) | |
| *G06V 10/764* | (2022.01) | |
| *G06V 10/776* | (2022.01) | |
| *G16H 30/20* | (2018.01) | |

(52) U.S. Cl.
CPC ............ *G06T 7/0012* (2013.01); *G06T 7/11* (2017.01); *G06V 10/22* (2022.01); *G06V 10/764* (2022.01); *G06V 10/776* (2022.01); *G16H 30/20* (2018.01); *G06T 2207/20021* (2013.01); *G06T 2207/20076* (2013.01); *G06T 2207/20081* (2013.01); *G06T 2207/20084* (2013.01); *G06T 2207/30096* (2013.01); *G06V 2201/03* (2022.01)

(58) Field of Classification Search
CPC .................... G06T 7/0012; G06T 7/11; G06T 2207/30096; G06V 10/764; G06V 2201/03
See application file for complete search history.

(56) References Cited

U.S. PATENT DOCUMENTS

| | | | |
|---|---|---|---|
| 2020/0105413 A1* | 4/2020 | Vladimirova | G16H 20/30 |
| 2020/0302603 A1* | 9/2020 | Barnes | G06T 7/0012 |
| 2021/0004650 A1* | 1/2021 | Frank | G06F 18/2415 |
| 2021/0090694 A1* | 3/2021 | Colley | G16H 20/10 |
| 2021/0142904 A1* | 5/2021 | Michuda | G16H 50/20 |
| 2021/0256699 A1* | 8/2021 | Wainrib | G06T 7/0012 |
| 2021/0327534 A1* | 10/2021 | Nicula | G16B 20/00 |
| 2021/0398617 A1* | 12/2021 | Finkle | G16B 40/20 |
| 2022/0076410 A1* | 3/2022 | Georgescu | G06T 7/0012 |
| 2022/0084660 A1* | 3/2022 | Georgescu | G06N 3/08 |
| 2022/0189150 A1* | 6/2022 | Bentaieb | G06V 20/698 |
| 2023/0030506 A1* | 2/2023 | Jaber | G06F 18/2413 |

* cited by examiner

*Primary Examiner* — Benjamin O Dulaney (57) ABSTRACT

Accurate tissue segmentation is performed without a priori knowledge of tissue type or other extrinsic information not found within the subject image, and may be combined with classification analysis so that diseased tissue is not only delineated within an image but also characterized in terms of disease type. In various embodiments, a source image is decomposed into smaller overlapping subimages such as square or rectangular tiles. A predictor such as a convolutional neural network produces tile-level classifications that are aggregated to produce a tissue segmentation and, in some embodiments, to classify the source image or a subregion thereof.

19 Claims, 3 Drawing Sheets

DIGITAL TISSUE SEGMENTATION AND MAPPING WITH CONCURRENT SUBTYPING

CROSS-REFERENCE TO RELATED APPLICATION

This is a continuation-in-part of U.S. Ser. No. 17/402,524, filed on Aug. 14, 2021, which is itself a continuation-in-part of U.S. Ser. No. 16/904,666, filed on Jun. 18, 2020, and also claims priority to, and the benefits of, U.S. Ser. No. 63/078,787, filed on Sep. 18, 2020. This application also claims priority to U.S. Ser. No. 63/331,265, filed on Apr. 15, 2022. The entire disclosures of the foregoing priority documents are hereby incorporated by reference.

FIELD OF THE INVENTION

The present invention relates, generally, to processing and automated segmentation and classification of medical images.

BACKGROUND

"Deep learning" approaches have been applied to a wide range of medical images with the objective of improving diagnostic accuracy and clinical practice. Many efforts have focused on images that are inherently small enough to be processed by convolutional neural networks (CNNs), or which can be downsampled to a suitable size without loss of fine features necessary to the classification task. In general, commonly used CNNs running on standard hardware can comfortably handle image sizes of 600×600 pixels or less; larger images entail complex architectures that are difficult to train, perform slowly, and require significant memory resources. Among the most challenging medical images to analyze computationally are digital whole-slide histopathology images, which are often quite large—10,000 to more than 100,000 pixels in each dimension. Their large size means that even traditional visual inspection by trained pathologists is difficult. To make such images amenable to CNN analysis, researchers have decomposed them into much smaller tiles that are processed individually. A probability framework is applied to the tile-level classifications to classify the slide. The most successful recent studies have achieved performance comparable to that of experienced pathologists.

A longstanding impediment to clinical adoption of machine-learning techniques is the inability of many such techniques to convey the rationale behind a classification, diagnosis or other output. Black-box models whose reasoning is opaque or impervious to retrospective analysis may pose clinical dangers that outweigh the benefits of a computational approach. Until recently, CNNs have fallen squarely within the black-box category, but techniques such as gradient-weighted class activation maps ("Grad-CAM") have pried the box open, highlighting the image regions important to a CNN classification.

While the ability to visualize regions of an image important to classification is useful, it does not necessarily address clinical acceptance. Grad-CAM images, for example, each represent a minuscule portion of the total slide area, Painstaking analysis of many such images could help validate the proposition that the CNN is "looking" where it should. But for any Oven slide classification, Grad-CAM cannot realistically illuminate its underlying basis; the Grad-CAM images are too small and a readable map of them superimposed on the slide would be impossibly large. Moreover, identifying which image regions attract the attention of a CNN does not reveal the underlying rationale for a classification—only the pixels on which the classification, whatever its basis, depended most strongly. But the CNN does process every pixel in the image. Attaching the highest classification importance to image regions of lower diagnostic significance does not necessarily undermine the validity of the classification.

More generally, the ability to visualize distinct tissue regions in a medical image can be important diagnostically whether or not an explicit classification is involved. Computational techniques for automatic "tissue segmentation" partition an image into segments corresponding to different tissue classes, e.g., whole organs or sub-regions of organs (such as liver or lung segments, or muscle groups). Areas with pathologies such as tumors or inflammation can also be isolated using segmentation. Traditionally, diagnoses have been based on manual measurement of lesion dimensions and their number in a medical image. More recently, the role of imaging has grown beyond diagnosis to include quantitative characterization of tissue volume or shape, chemical composition, and functional activity, and automated tissue segmentation has played an important part in this evolution. But segmentation techniques tend to be complex and computationally demanding, and may require knowledge of the imaged anatomical structure or other a priori information.

SUMMARY

Embodiments of the present invention provide approaches to accurate tissue segmentation that do not require a priori knowledge of tissue type or other extrinsic information not found within the subject image. Moreover, the approaches discussed herein may be combined with classification analysis so that diseased tissue is not only delineated within an image but also characterized in terms of disease type or subtype. The techniques may be applied even to very large medical images such as digital pathology slides, but are equally applicable to smaller images such as X-rays, mammograms, ultrasound images, and nuclear-medicine images (e.g., Mill and PET). In various embodiments, a source image is decomposed into smaller overlapping subimages such as square or rectangular tiles, which are sifted based on a visual criterion. The visual criterion may be one or more of image entropy, density, background percentage, or other discriminator. A classifier, such as a CNN an autoencoder or other classification tool for image data, produces tile-level classifications that are aggregated to produce a tissue segmentation and, in some embodiments, to classify the source image or a subregion thereof.

Overlapping subimages represents a useful data-augmentation expedient for training purposes, but also is found to enhance classification of test images and mapping accuracy, with the enhancement depending directly on the degree of overlap. In particular, the greater the degree of overlap, the greater will be the number of images that may contribute to the classification of any particular pixel, thereby potentially increasing the accuracy of the tissue segmentation.

In various embodiments, the same basic workflow is used both for segmentation and classification. The workflow involves first decomposing a candidate image into tiles whose size is optimized for segmentation and, separately, for subtyping if this is done; generating tile-level classification probabilities and combining these in accordance with a selection framework to produce a pixel-level segmentation mask and, optionally, a subtype classification. Even if image resolution and tile sizes differ between segmentation and subtyping tasks, the same routines may be used in both cases.

Average tile-level predictions from multiple models may be combined to make best use of limited training images. For example, multiple CNN models may be generated based on training images that have been grouped into overlapping subsets in the manner of cross-validation folds; tiles derived from each subset are used to train a separate CNN model. When a candidate image is analyzed, each tile derived from the image is examined by the ensemble of models. Averaging the resulting predictions reduces random error associated with the individual CNN models, enhancing the accuracy of the resulting segmentation. In addition, the tile-level predictions may be selected or combined so as to favor a particular similarity metric.

DESCRIPTION OF THE DRAWINGS

The foregoing discussion will be understood more readily from the following detailed description of the disclosed technology, when taken in conjunction with the following drawings, in which.

DESCRIPTION

Figure 1:
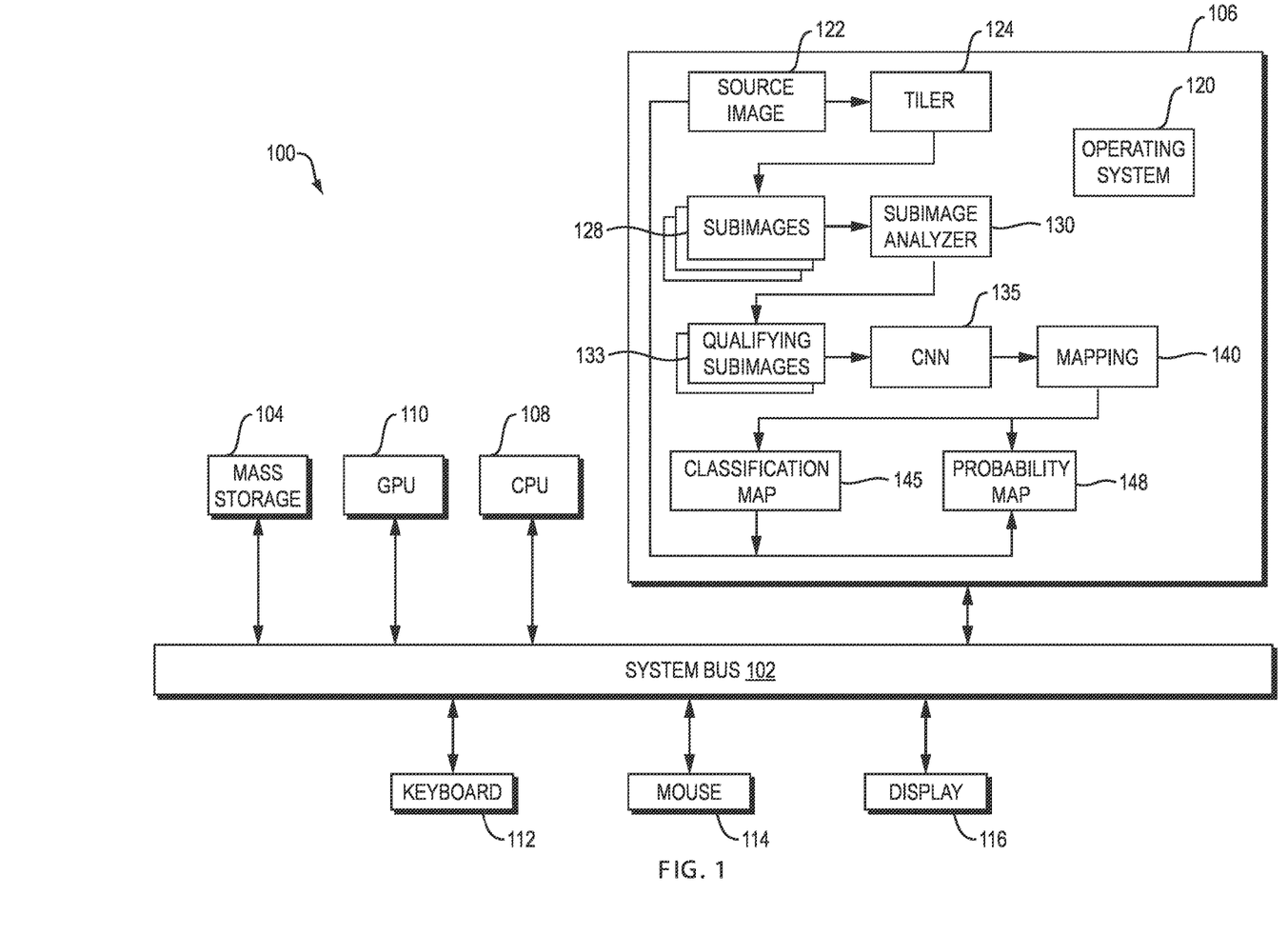
FIG. 1 schematically illustrates a representative hardware architecture according to embodiments of the invention.

Refer first to FIG. 1, which illustrates a representative system 100 implementing an embodiment of the present invention. As indicated, the system 100 includes a main bidirectional bus 102, over which all system components communicate. The main sequence of instructions effectuating the functions of the invention and facilitating interaction between the user and the system reside on a mass storage device (such as a hard disk, solid-state drive or optical storage unit) 104 as well as in a main system memory 106 during operation. Execution of these instructions and effectuation of the functions of the invention are accomplished by a central processing unit ("CPU") 108 and, optionally, a graphics processing unit ("GPU") 110. The user interacts with the system using a keyboard 112 and a position-sensing device (e.g., a mouse) 114. The output of either device can be used to designate information or select particular areas of a screen display 116 to direct functions to be performed by the system.

The main memory 106 contains instructions, conceptually illustrated as a group of modules, that control the operation of CPU 108 and its interaction with the other hardware components. An operating system 120 directs the execution of low-level, basic system functions such as memory allocation, file management and operation of mass storage devices 104. At a higher level, a source image 122, stored (e.g., as a NumPy array) in an image buffer that may be a partition of main memory 106, is processed by a tiler module 124 to produce a plurality of subimage portions (or "tiles") 128 of source image 122 based on a user-specified overlap factor. Tiles 128 may be stored in a storage device 104 along with coordinates specifying their locations in source image 122.

An analyzer 130 sifts subimages 128 according to a visual criterion, as described in greater detail below, to identify the subimages 133 that satisfy the criterion. The qualifying subimages 133 are analyzed by a predictor or classifier, e.g., a CNN 135 that has been trained for the classification task of interest to produce predictions (e.g., probability values) indicative of a classification. CNN 135 may be straightforwardly implemented without undue experimentation. Python/Keras code for a suitable five-layer CNN architecture may be found at https://github.com/stevenjayfrank/A-Eve, the contents of which are incorporated by reference herein. Alternatively, the classifier may be an autoencoder paired with a hyperplane classifier such as a multilayer perceptron or a support vector machine. The autoencoder learns a representation (encoding) for the sifted tiles at a dimensionality low enough for classification using a hyperplane classifier. To achieve dimensionality reduction, the autoencoder is trained to ignore insignificant data. See, e.g., Zeggada et al., "Multilabeling UAV images with Autoencoder networks," *Proc. of* 2017 *Joint Urban Remote SensingEvent*, DOI: 10.1109/JURSE.2017.7924544, the entire disclosure of which is hereby incorporated by reference. Other classifiers include random-forest classifiers, classifiers based on clustering (such as K-means or K-medoids), minimum-distance classifiers, maximum-likelihood classifiers, and decision-tree classifiers. For ease of presentation, the ensuing discussion presumes use of a CNN classifier, it being understood that alternatives known to those of skill in the art are within the scope of the invention.

CNN 135 computes a classification probability for each qualifying subimage 133. A mapping module 140 builds a classification map 145 by computing the average probability associated with each classified pixel across all subimages that include that pixel, or otherwise combining pixel-level probabilities as described below. So long as CNN 135 is reasonably well calibrated—i.e., the predicted probabilities correspond approximately to true likelihoods—the pixel-level probabilities will be accurate (and contributions from multiple tiles will reduce error). From classification map 145, mapping module 140 generates the probability map 148 based on the final probability value of each classified pixel and the color associated with that value. Because only part of the original source image may have associated probability levels (since, usually, not all subimages satisfy the visual criterion), it may be useful for probability map 148 to represent source image 122 as a gray scale (or line or other monochromatic) image with colors overlaid translucently where probabilities were obtained. This is straightforwardly implemented in accordance with well-known techniques.

For medical images, it may be desirable in some implementations to use two colors—one delineating regions of high interest and the other covering regions of moderate interest based on probability levels. This strategy draws initial attention to the regions where disease or abnormality is most likely present. If disease exists, the largest amount will probably be found in the high-interest regions. If none is found there, the reviewing clinician can move on to the regions of moderate interest. Combined with the ability to toggle between the probability map and a congruent display of the source image as described in the '265 application (and with translucent colors), this approach may ease the burden of reviewing an image without sacrificing the ability to conveniently inspect all relevant anatomy. On a touchscreen device, both images—the probability map and the congruent source image—may be stretched and squeezed even though only one image at a time is viewed.

For example, high-probability regions may be defined as those where prediction probabilities equal or exceed the mean probability of all tiles properly classified as disease tiles on a test set of images. Alternatively, the threshold may be set to maximize a parameter of interest, e.g., the precision of the high-probability regions. In some embodiments, all pixels whose probabilities (averaged over all tiles containing the pixel) equal or exceed the high-probability threshold are colored red. The low-probability threshold may be based on the standard deviation of probabilities assigned to the tiles properly classified as diseased on the test set. Typically the low threshold is one standard deviation below the high threshold, or may correspond to the decision boundary used for training. In some cases it may be lower than the decision boundary in order to reveal more potentially diseased tissue. In some embodiments, all pixels whose averaged probabilities fall between the low and high thresholds are colored yellow.

Classification map 145 and probability map 148 may be stored in memory 106 as data arrays, image files, or other data structure, but need not be distinct. Instead, probability map 148 may be generated directly from the source image (e.g., in grayscale format) and average (or otherwise combined) pixel-level classification probabilities as these are computed—i.e., the probability and classification maps may be the same map.

In one embodiment, tiler 124 generates subimage tiles 128 of specified dimensions from a source image 122 by successive identification of vertically and horizontally overlapping tile-size image regions. The Python Imaging Library, for example, uses a Cartesian pixel coordinate system, with (0,0) in the upper left corner. Rectangles are represented as 4-tuples, with the upper left corner given first; for example, a rectangle covering all of an 800×600 pixel image is written as (0, 0, 800, 600). The boundaries of a subimage of width=w and height=h are represented by the tuple (x, y, x+w, y+h), so that x+w and y+h designate the bottom right coordinate of the subimage.

Figure 2:
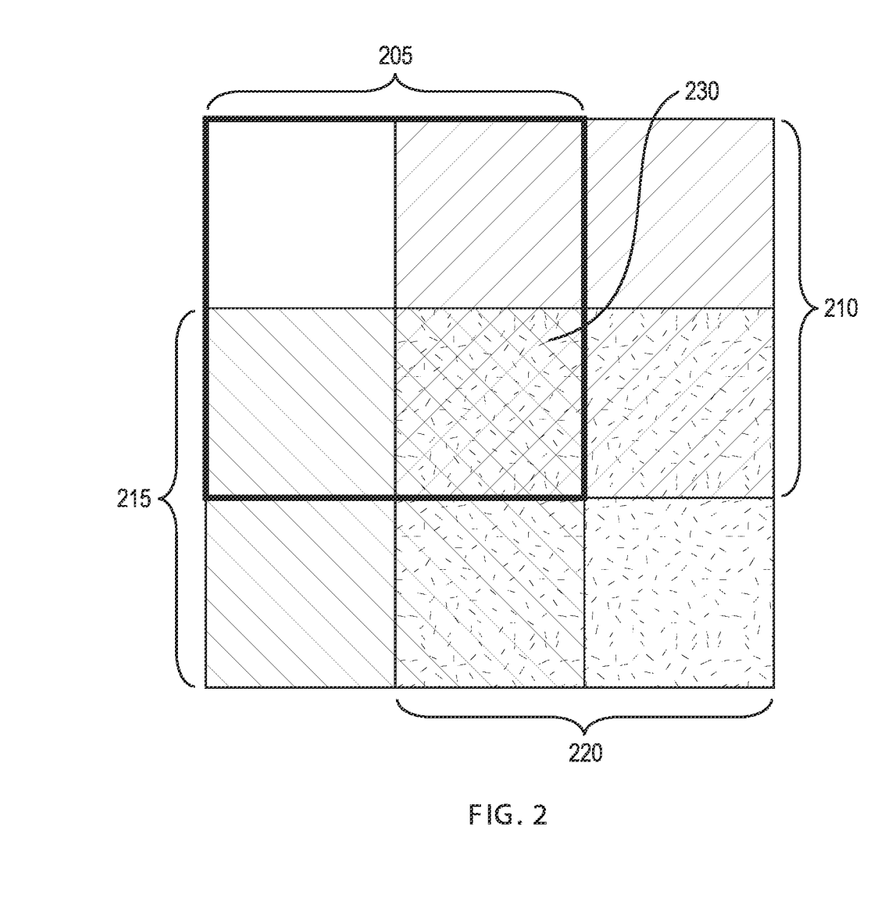
FIG. 2 illustrates two-dimensional overlap among subimages.

The tile overlap factor may be defined in terms of the amount of allowed overlap between vertically or horizontally successive subimages; hence, an overlap factor of ½ results in 50% vertical or horizontal overlap between consecutive subimages. This is illustrated in FIG. 2. Tile pairs 205, 210 and 215, 220 have 50% horizontal overlap (with the border of tile 205 being emphasized for clarity). In addition, tile pair 215, 220 has 50% vertical overlap with tile pair 205, 210. This two-dimensional overlap results in a central region 230 where all four tiles 205, 210, 215, 220 overlap and may contribute, by averaging or other combination, to a classification probability. The greatest number of overlapping images occupy the central region 230, which, as overlap increases, diminishes in size but increases in terms of the number of contributing subimages. More importantly, increasing overlap means that more of the area of any single tile will overlap with one or more other tiles, so that more pixels of any tile will receive probability contributions from other tiles with consequent reduction in classification error; consequently, if only a minority of tiles are misclassified, the effect of overlap by properly classified tiles will overwhelm the misclassification error and the resulting probability map will have high accuracy. Typical overlap factors exceed 50%, e.g., 60%, 70%, 80%, or even 90% or more along both dimensions.

The optimal tile size may be determined for a particular application by testing various tile sizes to find the best-performing size. Medical images, particularly very large (e.g., histology or pathology) images, may be preliminarily resealed to a smaller size. This permits tiles within the previously noted working range to cover an adequately large portion of the depicted anatomy to provide accurate classifications. At the same time, the resealed image must preserve sufficient anatomic detail. These steps—initial image resealing followed by trials at multiple tile sizes—provide two "knobs" for overall optimization, which may be achieved for a given application without undue experimentation. See, e.g., Frank, "Resource-frugal classification and analysis of pathology slides using image entropy," *Biomedical Signal Processing and Control*, 66, 102388 (April 2021), which is incorporated by reference herein. As described below, the image rescalings optimal for segmentation and classification tasks may differ.

In some cases, the resolution needed for a useful segmentation map is smaller than the optimal tile size obtained for the largest usable source image—i.e., it is not possible to increase the mapping resolution by using a larger source image. In such cases, the source image may be decomposed into tiles corresponding to the necessary mapping resolution, and instead of analyzing these small tiles directly, upscaling them to a size at which CNN 135 performs efficiently. As long as the critical spatial relationships among visual features and their consistuents are preserved, the coarser image resolution at the upscaled tile size will not impede accurate classification. Once the upscaled tiles are analyzed and mapping tiles identified, the map may be assembled using the corresponding original (smaller) tiles to achieve the desired resolution. Upscaling may be performed using any of a variety of conventional techniques including nearest-neighbor interpolation, bilinear and bicubic algorithms, edge-directed interpolation, Fourier-transform methods, vectorization, or using a CNN that has been trained for upscaling on the subject matter of the image.

Once the tiles are generated, they are sifted in accordance with a visual criterion with the objective of eliminating tiles that are not meaningful for classification. In one embodiment, the visual criterion is image entropy. From the purview of information theory, image entropy represents the degree of randomness (and therefore information content) of the image pixel values, just as the entropy of a message denotes (as a base-2 log) the amount of useful, nonredundant information that the message encodes:

$$H = -\sum_k p_k \log_2(p_k)$$

In a message, $p_k$ is the probability associated with each possible data value k. For an image, local entropy is related to the complexity within a given neighborhood, sometimes defined by a structuring element such as a circular or square region, or the entire image. Thus, the entropy of a grayscale image (or one channel of a color (e.g., RGB) image) can be calculated at each pixel position (i,j) across the image. To the extent that increasing image entropy correlates with increasingly rich feature content captured in the convolutional layers of a CNN, it provides a useful basis for selecting tiles. In one implementation, only those tiles whose entropies equal or exceed the entropy of the whole image are retained. Although no subimage will contain as much information content as the original, a subimage with comparable information diversity may pack a similar convolutional punch, so to speak, when processed by a CNN. In some embodiments, depending on the distribution of tile entropies, the discrimination criterion may be relaxed in order to increase the number of qualifying tiles. Because of the logarithmic character of the entropy function, even a slight relaxation of the criterion can result in many more qualifying tiles. For example, the criterion may be relaxed by 1% (to retain tiles with image entropies equal to or exceeding 99% of the source image entropy), or 2%, or 3%, or 4%, or 5%, or up to 10%. Tile sifting using image entropy is further described in Frank et al., "Salient Slices: Improved Neural Network Training and Performance with Image Entropy," *Neural Computation*, 32(6), 1222-1237 (2020) (hereafter "Frank et al."), which is incorporated by reference herein.

Another suitable approach to tile sifting uses a background threshold criterion, retaining only tiles with a proportion of background below a predetermined limit. Images of pathology slides, for example, typically have white or near-white backgrounds. But the tissue of interest may also have white features, gaps or inclusions. Hence, while the presence of any background can adversely affect training and classification accuracy, eliminating all tiles containing regions that might potentially be background risks discarding anatomy critical to classification. Hence, the minimum background threshold is generally set at 50% or higher, e.g., 60%, 70%, 80%, or even 90%; the optimal threshold depends on the amount of background-shaded area that may appear in non-background regions.

One approach to background identification and thresholding is to convert a colored tile to grayscale and count pixels with color values corresponding to background, e.g., white or near-white pixels. For example, an RGB image has three color channels and, hence, three two-dimensional pixel layers corresponding to red, blue, and green image components. In an eight-bit grayscale image, a pixel value of 255 represents white. To allow for some tonal variation from pure white arising from, for example, the source imaging modality, any pixel in any layer with a value above, e.g., 240 may be considered background. Summing the number of such pixels and dividing by the total number of pixels yields the background fraction. Only tiles with background fractions below the predetermined threshold (typically from 0.1 to 0.5, depending on the image characteristics) are retained.

This approach may not be suitable for tiles based on images that have been subjected to stain normalization, which reduces the color and intensity variations present in stained images from different laboratories, since the background may be shifted too far away from white. In such cases, it may be preferable to threshold tiles based on the number of identically valued pixels rather than their proximity to white or black extremes. Pixel value frequency may be obtained, for example, as an occurrence list (using, e.g., the NumPy "unique" function) specifying pixel values and their populations within the tile, and if the maximum occurrence level exceeds the threshold fraction, the tile is rejected. In some embodiments, the first n occurrence levels are summed and compared to the threshold, where n is desirably large enough to ensure that all pixels corresponding background regions are included in the count. The value of n may be straightforwardly determined by, for example, examining background regions of representative source images or tiles determine the number of associated pixel values (e.g., once again using the NumPy "unique" function), or alternatively, by simply experimenting with candidate values and examining the tiles characterized as background and non-background, selecting the value that excludes all background tiles and a minimum number of non-background tiles. In practice, n typically ranges from 2 to 5.

Still another suitable visual criterion is image density. If regions of interest for classification purposes are known to have image densities above a minimum, that minimum may be used as a discrimination threshold to sift tiles. In yet other embodiments, the visual criterion is functionally defined—e.g., discriminating between a sample and the background glass slide—and may be implemented using machine learning, e.g., a neural network trained to make the functional distinction.

With renewed reference to FIG. 1, once tiles have been sifted and qualifying tiles 133 identified and stored in volatile and/or nonvolatile storage, they are used either to train CNN 135 or are presented to a trained CNN as candidate images for classification. The output of CNN 135 is generally a classification probability. In some instances, the classification is binary (e.g., cancerous or benign, adenocarcinoma or squamous cell carcinoma, etc.) and the decision boundary lies at 0.5, so that output probabilities at or above 0.5 correspond to one classification and output probabilities below 0.5 reflect the other classification. In other instances, there are multiple output classifications and a "softmax" activation function maps CNN output probabilities to one of the classes.

For ease of illustration, consider binary classification of a histology slide that may contain either or both of two types—"type 1" and "type 2"—of cancerous tissue. The slide, possibly after initial resizing (e.g., downsampling to a lower resolution), is decomposed into overlapping subimages 133, which are sifted as described above. The sifted subimages are processed by CNN 135, which has been trained to distinguish between type 1 and type 2 cancers. CNN 135 assigns a classification probability p to each subimage, with probabilities in the range $0.5 \leq p < 1.0$ corresponding to type 1 and probabilities in the range $0 < p < 0.5$ corresponding to type 2. Each individual subimage may contain only a small amount of type 1 or type 2 tissue, yet the entire subimage receives a unitary probability score. As a result, the score assigned to an individual subimage may be skewed so as, for example, to ignore type 1 and/or type 2 tissue that is present but in too small a proportion to trigger the proper classification. With sufficient overlap and pixel-level averaging, this classification error will be mitigated as overlapping subimages containing progressively greater proportions of the type 1 and/or type 2 tissue contribute to the average pixel-level probabilities.

In various embodiments, a pixel-level probability map is defined to reflect average probabilities across all classified subimages. For example, in Python, a 3D m×n×d NumPy array of floats may be defined for an m×n source image, with the parameter d corresponding to the number of classified subimages (which were identified as satisfying a visual criterion). At each level d, the array is undefined or zero except for the region corresponding to one of the classified subimages, and all array values in that 2D region are set to the classification probability computed for the subimage. The probability map is an m×n array, each value [i,j] of which is equal to some combination of all nonzero values [i,j,d:] of the 3D array, e.g., the average of all nonzero values [i,j] over the d-indexed axis. The greater the degree of subimage overlap, the deeper the number of nonzero values will extend through the d-indexed axis and, therefore, the more probability values (from overlapping subimages) that will contribute to the combined value at any point of the probability map, enhancing classification accuracy for that point. Points in the probability map corresponding to points in the 3D array with no nonzero values over the d-indexed axis—i.e., where the source image lacked sufficient image entropy to generate a subimage satisfying the criterion—may be left undefined.

The probability map, therefore, is a map of pixelwise classification probabilities. The probability map may be dense (i.e., have values over most of the source image) or sparse (with relatively few defined values) depending on the amount of visual diversity in the source image and the number of qualifying tiles left after sifting. Pathology images, for example, vary markedly in visual density and may be dense or sparse. The probability map may be color-coded, with different colors assigned to discrete probability ranges. For example, the color coding may follow the visible spectrum, with low probabilities corresponding to blue and high probabilities represented by red, and intermediate probability ranges assigned to intermediate spectral colors. The number of colors used (i.e., how finely the probability range of 0 to 1 is partitioned) depends on the classification task and how meaningful small probability gradations are for the viewer. This is discussed further below. A tissue segmentation may alternatively take the form of a binary mask that, e.g., is black for all normal tissue areas and white or transparent for all abnormal tissue regions. Such a mask is considered a probability map as the latter term is used herein.

The classification need not be binary. For example, CNN 135 may be trained with subimages 128 corresponding to three types of tissue, e.g., normal tissue and two distinct types of malignant tumor. Probabilities may be computed according to, for example, a softmax activation function. Pixel-level probabilities from overlapping tiles can be averaged as described above or, because the softmax function is a ratio of exponentials, the mean may be weighted or otherwise adjusted accordingly. More simply, the softmax probabilities associated with each pixel may be summed and the class label corresponding to the largest sum (identified, for example, using the argmax( ) function to select a label index) assigned to the pixel with, for example, a probability of 1. Following these assignments, classification map 145 will have pixels with class labels and associated probability values of 1, and the remaining pixels will have probability values of 0.

If the image to be analyzed is known to contain only one of multiple classifications, the dominant label among labeled pixels—that is, the label with the most pixel assignments—may be identified, and in some implementations, only pixels having that label are mapped in probability map 148. If the subimage size is small enough, the dominant label can be assessed at a subimage level, and the pixels of classification map 145 corresponding to those of each subimage classified with the dominant label are assigned a probability of 1. These pixels may be assigned a monochromatic color and translucently superimposed over the grayscale version of source image 122 to generate the final probability map 148. Thus, in this case, combining class probabilities means assigning a value of 1 to any pixel intercepted by any number of tiles having the dominant label (and assigning a value of 0 otherwise). Examples of tissue segmentations generated in this fashion are illustrated in Frank, "Tissue Segmentation from Whole-Slide Images Using Lightweight Neural Networks," *Research Square*, DOI: 10.21203/rs.3.rs-122564/v1 (Dec. 15, 2020), the entire disclosure of which is hereby incorporated by reference.

If the image might validly have multiple classifications, on the other hand, these classifications may be mapped in different colors. Alternatively, multiple probability maps each colored to show one of the classifications may be generated.

For example, CNN 135 may be trained to discriminate among multiple tumor types, but suppose it is known that any malignant histology sample can contain only one type of tumor. In that case, the image of a new sample may be tiled and sifted in accordance with a visual criterion, and the sifted tiles presented to CNN 135 for classification. Due to error, the resulting classifications may incorrectly include more than one tumor type. If CNN 135 has been properly trained, the correct classification type will predominate among tiles classified in one of the malignant categories (as opposed to classification as normal tissue). The minority tiles may therefore be ignored and only the dominant tumor tiles mapped. Since the minority tiles are excluded altogether rather than being averaged with the dominant tiles, there is no need for probability-based color coding; the dominant tiles may be overlaid in a single color on a grayscale version of the sample image, producing a tissue segmentation indicating the location and type of tumor in the sample—that is, the union of all dominant tiles will be colored monochromatically in probability map 148.

Another approach to distinguishing among tumor types is to separate the segmentation and classification tasks. A first CNN may be trained to distinguish generally between diseased and undiseased (e.g., tumor and non-tumor) tissue. A second CNN may be trained to distinguish among two or more disease subtypes in tissue known to be diseased. This approach recognizes that the image and tile sizes for distinguishing diseased and undiseased tissue may be different from the image and tile sizes optimal for classifying disease subtypes. In one implementation, segmentation training images are prepared using segmentation masks that occlude undiseased portions of an image. These "ground truth" masks may be generated manually, by trained pathologists, or in an automated fashion. The masks allow the diseased portions of a medical image to be extracted, and tiles from just this region may be prepared as described above (e.g., without regard to a visual criterion). The maximum and minimum entropies associated with these tiles may be obtained and noted, and used as described below. Next, the segmentation masks are inverted and comparative tiles generated from the undiseased image regions. The tiles drawn from diseased and undiseased regions are treated as separate classes and used to train a segmentation CNN. This procedure is repeated over multiple images scales and tile sizes to find an optimal combination that produces best (e.g., highest accuracy or lowest loss) CNN performance in distinguishing disease tiles from non-disease tiles. The best-performing segmentation CNN, thus trained using the optimal combination of image rescaling and tile size, may then be used to generate segmentations from candidate images.

The maximum and minimum entropies of tiles derived from disease-only images may be treated as boundaries or "rails" within which tiles from a candidate image must fall in order to qualify as usable. Sifting in accordance with this criterion preliminarily eliminates tiles unlikely to correspond to diseased tissue. Thus, a medical image to be classified and/or mapped may be downsampled, tiled, and the tiles sifted using the previously established entropy boundaries, which serve as a preprocessing check to exclude normal tissue tiles that might have been misclassified as disease tiles.

A similar procedure of optimization and training is undertaken to train a CNN to classify disease subtypes. Here only tiles drawn from disease regions are used for training. The training images are organized into sets corresponding to the subtypes of interest and the ground-truth segmentation masks used to isolate the disease regions. The different subtypes are treated as different classes for training purposes, and tiles drawn from the disease regions are used to train a CNN to distinguish among the subtypes. The optimal image rescaling and tile size for classification may or may not be the same as those supporting segmentation.

While simple classification scores (accuracy, area under receiver operating curve (AUROC), F1 score, etc.) are readily used to assess the quality of a classification model, the success of a segmentation is typically judged using a similarity metric quantifying how close a predicted segmentation is to the ground truth. The most common metric, intersection over union ("IoU") or Jaccard score, quantifies the degree of overlap between the prediction P and the ground truth T:

$$IoU = \text{Jaccard score} = \frac{P \cap T}{P \cup T}$$

Precision (or specificity) represents the proportion of pixels classified as positive (e.g., as disease pixels) that are, in fact, positive while recall (or sensitivity) corresponds to the proportion of all positive pixels correctly classified as such. In terms of true positives (IP), false positives (FP), and false negatives (FN), $$\text{Precision} = \frac{TP}{TP + FP}$$

$$\text{Recall} = \frac{TP}{TP + FN}$$

Which metric is most important depends on the application. For safety in clinical applications, recall may be most critical to ensure that nothing of significance is missed. If precision is too low, however, the segmentation loses its diagnostic utility as too much undiseased tissue is marked as diseased. The IoU score reflects a combination of these considerations.

To create a segmentation from a candidate image, the image is rescaled and tiled according to the optimized parameters used for training, and the tiles are sifted using the entropy rails established for the diseased regions during training. Tiles classified as diseased may be mapped as discussed above; the union of all such tiles, as mapped, constitutes the tissue segmentation, which may be overlaid onto the original image or may instead be output as a binary mask. For example, in a binary classification, the union of all abnormal tissue tiles may overlaid onto the original image as white or transparent, with the remainder of the image rendered as black. Whether white/transparent or colored, the union of overlapping tiles represents an approximation of the abnormal tissue region—i.e., a tissue segmentation. Alternatively, the classification probabilities for overlapping tiles may be combined at a pixel level as described above, with the black and white (or transparent) image regions rendered at a pixel (rather than a tile) level.

Due to the tile geometry, the segmentation region will have stepped edges that appear jagged. The edges may be smoothed with a median or other smoothing filter. (It should be noted that smoothing may be beneficially applied to any type of probability map described herein.) Furthermore, tile size limits the contour accuracy of the probability map; the larger the tile size, the more the edges of the map will spill over into the oppositely classified tissue region (e.g., into normal tissue). From a clinical perspective such overinclusiveness is perhaps to be preferred to the alternative, but in any case, the tile size is generally dictated by what works best for the overall task of classifying tissue. To compensate for this spillover effect, it is possible to apply isomorphic shrinkage to the mapped regions; the larger the tile size, the greater the degree of shrinkage that may be applied before or after smoothing. The optimal amount of image resizing for a given tile size is straightforwardly obtained without undue experimentation.

In some circumstances, it may be preferred to utilize a plurality of CNNs in sequence, e.g., to detect two different types of tissue. For example, perineural invasion by malignant tumor cells has been reported as an independent indicator of poor prognosis in cancers. Visually, it may be desirable to detect regions composed of nerve and tumor cells, e.g., where the tumor has infiltrated a nerve. Most straightforwardly, CNN 135 is trained to distinguish among nerve tissue, tumor tissue, and tissue that is neither nerve nor tumor; this may be accomplished using a categorical cross-entropy loss function and softmax activation. Inferior performance may be obtained, however, if the background tissue is heterogeneous and contains regions that are too visually similar to one of the target tissues. In this case, it may be beneficial to train a first CNN 135 to distinguish between one of the target tissues and background tissue, and a second CNN 135 to distinguish between the two target tissues. Applying the first CNN 135 to tiles derived from the original image will eliminate most of the background tissue, and subsequently applying the second CNN 135 to the surviving tiles will identifiy, inter alia, regions where the two target tissues are adjacent. Similarly, a CNN trained for three-way classification among two tumor types and background tissue may not adequately discriminate between the tumor types, particularly if the visual differences therebetween are subtle. Thus, a first CNN may be used to segregate tiles containing either tumor type from tiles containing background tissue, and the second CNN may analyze the tumor tiles to distinguish between the two tumor types. The two CNNs may have different architectures, e.g., the first CNN may have only a few (e.g., five) convolutional layers while the second CNN may have a more complex design (e.g., a residual network such as ResNet50, VGG16, Inception, etc.). Any number of identical or heterogeneous CNNs may be staged in this pipeline fashion to reduce a difficult multi-class classification problem to a sequence of more tractable binary classifications, similar to separating classification from subtyping tasks. Once again, either or both CNNs may be replaced with a different classifier, such as an autoencoder paired with a hyperplane classifier.

In a similar vein, an object-detection algorithm may be used to identify candidate regions corresponding to a tissue type of interest and a predictor, trained to distinguish among tissue types or subtypes, then used to select among the candidate regions. Object-detection algorithms include RCNN, Fast RCNN, Faster RCNN, Mask-RCNN, pyramid networks, YOLO, and newer YOLO versions v1-v5. Typically, object-detection algorithms predict the dimensions and locations of bounding boxes surrounding objects that the algorithm has been trained to recognize. Bounding boxes having probability scores below a threshold may be dropped. While object-detection algorithms have proven themselves capable of distinguishing among clearly different object types, they may have more difficulty distinguishing among tissue types whose differences are subtle, or where an image has limited information content. For example, chest X-rays may reveal one or more of numerous conditions such as atelectasis, consolidation, pleural effusion, pulmonary fibrosis, aortic enlargement, cardiomegaly, etc. These conditions may share various visual similarities in an X-ray image, which is not only grayscale but may have limited resolution. Similarly, mammograms may contain potentially malignant masses that are difficult to distinguish visually, given limited resolution and the absence of color, from fibrous breast tissue. In such cases, it may be useful to first apply an object-detection algorithm trained to recognize various chest conditions or potentially malignant masses. Then, after eliminating overlapping bounding boxes generated by the object-detection algorithm, the source-image regions defined by the bounding boxes that remain may be tiled and the tiles analyzed by a predictor (e.g., a CNN) trained to distinguish among tissue types or between a target tissue type and normal tissue. In this way, object-detection performance may be enhanced by identifying and discarding spurious bounding boxes, e.g., those for which the average classification over tiles generated therefrom (which may or may not be sifted) does not exceed a threshold—for example, the predictor's training decision boundary. Thus, in the case of a chest X-ray, the predictor may be trained to distinguish a particular condition from all other conditions, directly enhancing the predictive capability of the object-detection algorithm; or may instead be trained to distinguish between a particular condition and chest tissue not exhibiting that condition. In the case of a mammogram, the predictor may be trained to distinguish between potentially malignant masses and fibrous tissue.

In some embodiments, because an ensemble of models may produce more accurate results than a single model by eliminating some of the random error associated with each model of the ensemble, a plurality (i.e., two or more) predictors trained on different sets of images is employed. The different sets of images may be completely different, i.e., each set may consist of images not found in any other set. In other cases, the sets have some images in common in the manner of cross-validation folds. For example, each training set may include a collection of training images and a (usually smaller) collection of validation images; as a predictor is trained, performance is gauged against tiles derived from the validation images. In such cases, the sets may be organized so that they have training images in common but no validation images in common. The number of training images any training set has in common with any other training set may be capped (e.g., at 10%, 20%, 25%, or 30%) to avoid excessive redundancy, i.e., so the predictors trained on the different training sets exhibit different classification behavior.

Figure 3:
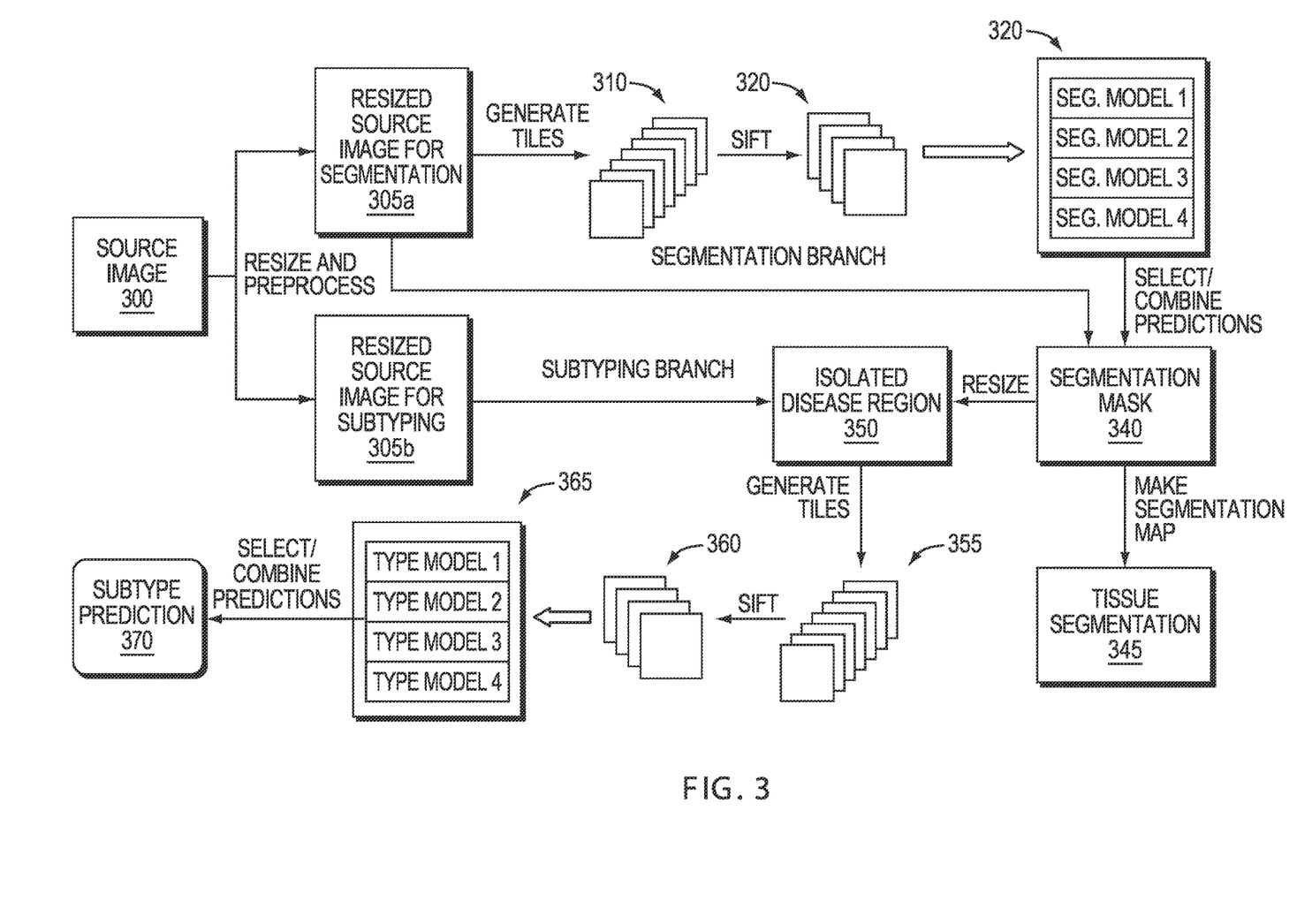
FIG. 3 schematically depicts a workflow according to embodiments of the invention.

FIG. 3 illustrates concurrent segmentation and subtyping in accordance with embodiments of the invention. With reference to FIGS. 1 and 3, a source medical image 300 is resized to an optimal size 305a for segmentation and also to an optimal size 305b for subtyping. The images 305a, 305b may be stored in one or more image buffers of main memory 106. In the segmentation processing branch, tiles 310 are generated from the resized source image 305a in accordance with a specified overlap, and then sifted by subimage analyzer 130 to produce a sifted tile set 320. For example, the tiles 310 may be sifted using entropy rails established for the type of medical image and tissue type under study. The sifted tiles 320 are presented to a plurality of predictors 330 that have been trained on different training sets as described above. In particular, the predictors 330 (indicated as Segmentation Models 1-4 in the figure, though there may be any suitable number of predictors) have been trained to distinguish between or among tissue types, e.g., between diseased and undiseased tissue.

Assuming for illustrative purposes that the tissue types are diseased and undiseased (e.g., tumor and non-tumor) tissue, each of the predictors 330 analyzes each of the tiles and produces a prediction (e.g., a probability) whether the tile is diseased or undiseased. The prediction probabilities are selected or combined as discussed in detail below to produce a single prediction classifying the tile. Once all of the tiles 320 have been classified, the classifications are used to produce a binary segmentation mask 340. The regions corresponding to tiles classified as diseased tissue, for example, can simply be combined in a union operation to form the white or transparent portion of the mask 340, or pixel-level classification probabilities can be derived from the union of tiles as described above, with pixels classified as diseased forming the white or transparent mask portion. The mask 340 may be applied to the resized source image 305a to produce a tissue segmentation 345. For example, regions of the source image 305a corresponding to the white or transparent portion of the mask 340 may be highlighted, colored, or otherwise distinguished from the rest of the image 305a in the tissue segmentation 345.

In the subtyping branch, the segmentation mask 340 is resized as necessary to conform dimensionally to the resized source image 305b, and is then applied to the source image 305b to occlude all regions thereof that have been classified as undiseased. Tiles 355 are generated from the isolated disease region 350 at a desired degree of overlap. These may be sifted to exclude tiles with too much background, but since the disease region 350 has been defined based on tiles that have already been classified, sifting may be minimal or omitted entirely. The sifted tiles 360 are applied to one or more predictors 365 (e.g., Type Models 1-4) that have been training to distinguish among subtypes. For example, Type Models 104 may have been trained on different training sets. The output of the predictor 365, or the averaged predictions of multiple predictors 365, provide the subtype prediction 370.

It has been found that for some applications, the spread among predictions produced by predictors trained for the same classification task on different training sets may indicate a degree of uncertainty in the reliability of the prediction. For example, a prediction may have a high confidence level if the the difference between maximum and minimum prediction probability values (ranging from 0 to 1) is less than 0.25, or less than 0.2, or less than 0.15; whereas a spread exceeding 0.3, 0.4 or 0.5 may correspond to a low confidence level due to the greater uncertainty. The exact values depend on various factors including the size of the training sets and the nature of the classification task, but are straightforwardly determined empirically without undue experimentation.

For segmentations, it has been found, surprisingly, that a desired similarity metric can be favored depending on the manner in which the ensemble predictions are handled. Averaging predictions across models maximizes Jaccard score, yielding segmentations that balance precision and recall. Selecting the maximum prediction for each tile favors recall. A high recall score ensures that Most or all of the diseased region is made visible in the segmentation. Selecting the minimum prediction for each tile favors precision. The ability to bias a segmentation to emphasize a desired performance parameter represents a substantial advantage of the ensemble technique in producing segmentations.

In general, it is noted that computers typically include a variety of computer-readable media that can form part of system memory and be read by the processing unit. By way of example, and not limitation, computer-readable media may take the form of volatile and/or nonvolatile memory such as read-only memory (ROM) and random access memory (RAM). A basic input/output system (BIOS), containing the basic routines that help to transfer information between elements, such as during start-up, is part of operating system 120 and is typically stored in ROM. RAM typically contains data and/or program modules that are immediately accessible to and/or presently being operated on by CPU 110. Operating system 110 may be or include a variety of operating systems such as Microsoft WINDOWS operating system, the UNIX operating system, the LINUX operating system, the MACINTOSH operating system, the APACHE operating system, or another operating system platform.

Any suitable programming language may be used to implement without undue experimentation the analytical functions described above and in the attached paper. Illustratively, the programming language used may include without limitation, high-level languages such as C, C++, C#, Java, Python, Ruby, Scala, and Lua, utilizing, without limitation, any suitable frameworks and libraries such as TensorFlow, Keras, PyTorch, or Theano. Further, it is not necessary that a single type of instruction or programming language be utilized in conjunction with the operation of the system and method of the invention. Rather, any number of different programming languages may be utilized as is necessary or desirable. Additionally, the software can be implemented in an assembly language and/or machine language.

CPU 108 may be a general-purpose processor, e.g., an INTEL CORE i9 processor, but may include or utilize any of a wide variety of other technologies including special-purpose hardware, such as GPU 110 (e.g., an NVIDIA 2070), a microcontroller, peripheral integrated circuit element, a CSIC (customer-specific integrated circuit), ASIC (application-specific integrated circuit), a logic circuit, a digital signal processor, a programmable logic device such as an FPGA (field-programmable gate array), PLD (programmable logic device), PLA (programmable logic array), smart chip, or any other device or arrangement of devices that is capable of implementing the steps of the processes of the invention. In some embodiments, all of the operations—decomposing a source image (typically downscaled if the original is very large, e.g., a "whole slide" pathology image) into tiles, sifting the tiles in accordance with a visual criterion, gnerating classification probabilities for the sifted tiles, and creating a segmentation map) are performed on a single device, e.g., a mobile device such as a tablet or "smart phone" implementing, for example, the iOS operating system supplied by APPLE Inc. or the ANDROID operating system supplied by GOOGLE Inc. In other embodiments, some operations (such as CNN analysis of tiles) may be performed by an external device, such as a "cloud" server in communication, via the interne, with a local device. For example, a source image may be rescaled by one cloud server, the rescaled (smaller) image inspected on a local device, and the analysis and map generation performed on a different cloud server. The distribution of functionality among devices is arbitrary and may depend on design preference and constraints.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of computationally generating a segmentation from a source digital image comprising a plurality of tissue types, the method comprising the steps of:
    computationally training each of a plurality of predictors to distinguish among tissue types, each of the predictors being trained using an associated training set of images, each of the associated training sets differing at least in part from the other associated training sets;
    computationally generating a plurality of overlapping subimage regions of the source image;
    computationally classifying at least some of the subimage regions by generating tissue-type predictions using each of the trained predictors;
    for each of the classified subimage regions, applying a function to the corresponding predictions to produce a final prediction;
    computationally combining, for each pixel of the source image contained within a classified subimage region, the final predictions corresponding to all of the subimage regions containing the pixel; and
    computationally generating the segmentation based at least in part on the pixelwise combined predictions.

2. The method of claim 1, wherein the function is selected to maximize a similarity criterion.

3. The method of claim 2, wherein the similarity criterion is one of Jaccard score, recall or precision.

4. The method of claim 3, wherein the similarity criterion is Jaccard score and the function is averaging the predictions of each of the trained predictors.

5. The method of claim 3, wherein the similarity criterion is precision and the function is selecting a minimum of the predictions of each of the trained predictors.

6. The method of claim 3, wherein the similarity criterion is recall and the function is selecting a maximum of the predictions of each of the trained predictors.

7. The method of claim 1, further comprising the steps of:
    using the segmentation to define one or more image regions corresponding to a first tissue type; and
    analyzing the defined one or more image regions with a predictor trained to distinguish among subtypes of the first tissue type; and
    based on the analysis, classifying the subtype of the defined one or more image regions.

8. The method of claim 7, wherein the similarity criterion is precision and the function is selecting a minimum of the final predictions.

9. The method of claim 1, further comprising the step of computationally sifting the subimage regions in accordance with a visual criterion.

10. The method of claim 1, further comprising the step of detecting an unreliable prediction based on a difference between minimum and maximum tissue-type predictions for at least some of the subimage regions.

11. An image-processing system for computationally generating a segmentation from a source digital image comprising a plurality of tissue types, the system comprising:
    a processor;
    a computer memory;
    a first image buffer for storing a source image;
    a tiling module for generating overlapping subimage regions of the source image;
    a plurality of predictors each trained using an associated training set of images, each of the associated training sets differing at least in part from the other associated training sets, the processor being configured to (i) apply the predictors to at least some of the subimage regions to produce tissue-type predictions therefor, (ii) apply a function to the corresponding predictions to produce a final prediction for each said subimage region, and (iii) combine, for each pixel of the source image contained within each said subimage region, the final predictions corresponding to all of the subimage regions containing the pixel; and a mapping module, executed by the processor, for computationally generating the segmentation based at least in part on the pixelwise combined predictions.

12. The system of claim 11, wherein the function is selected to maximize a similarity criterion.

13. The system of claim 12, wherein the similarity criterion is one of Jaccard score, recall or precision.

14. The system of claim 13, wherein the similarity criterion is Jaccard score and the function is averaging the predictions of each of the trained predictors.

15. The system of claim 13, wherein the similarity criterion is precision and the function is selecting a minimum of the predictions of each of the trained predictors.

16. The system of claim 13, wherein the similarity criterion is recall and the function is selecting a maximum of the predictions of each of the trained predictors.

17. The system of claim 12, wherein the similarity criterion is precision and the function is selecting a minimum of the final predictions.

18. The system of claim 11, further comprising a predictor trained to distinguish among a plurality of subtypes of a first tissue type and, based on the analysis, classify the subtype of portions of the segmentation containing the first tissue type.

19. The system of claim 11, wherein the processor is further configured to detect an unreliable prediction based on a difference between minimum and maximum tissue-type predictions for at least some of the subimage regions.

* * * * *